United States Patent
Clower et al.

(10) Patent No.: US 10,850,005 B2
(45) Date of Patent: Dec. 1, 2020

(54) MENISCAL REPAIR ADHESIVE

(71) Applicant: Arthrex, Inc., Naples, FL (US)

(72) Inventors: Dottie M. Clower, Pittsburgh, PA (US); Eric J. Beckman, Aspinwall, PA (US); Bradd N. Picone, Pittsburgh, PA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/397,002

(22) Filed: Apr. 29, 2019

(65) Prior Publication Data

US 2020/0085998 A1     Mar. 19, 2020

Related U.S. Application Data

(63) Continuation of application No. 15/252,275, filed on Aug. 31, 2016, now abandoned.

(60) Provisional application No. 62/211,953, filed on Aug. 31, 2015.

(51) Int. Cl.
| | |
|---|---|
| *A61L 27/18* | (2006.01) |
| *C08L 83/08* | (2006.01) |
| *C08L 91/00* | (2006.01) |
| *A61L 24/04* | (2006.01) |

(52) U.S. Cl.
CPC ............. *A61L 27/18* (2013.01); *A61L 24/046* (2013.01); *C08L 83/08* (2013.01); *C08L 91/00* (2013.01); *A61L 2400/06* (2013.01); *A61L 2430/06* (2013.01); *A61L 2430/10* (2013.01)

(58) Field of Classification Search
None
See application file for complete search history.

(56) References Cited

U.S. PATENT DOCUMENTS

| | | | | | |
|---|---|---|---|---|---|
| 4,127,515 | A | * | 11/1978 | MacRae | C08G 18/4833 106/10 |
| 4,548,954 | A | * | 10/1985 | Smith | C08J 9/0061 134/40 |
| 4,806,572 | A | * | 2/1989 | Kellett | A61K 8/0208 424/401 |
| 2004/0170597 | A1 | * | 9/2004 | Beckman | A61K 31/785 424/78.27 |
| 2004/0170670 | A1 | * | 9/2004 | Smith | A47K 7/02 424/443 |
| 2005/0013793 | A1 | * | 1/2005 | Beckman | C08G 18/12 424/78.27 |
| 2006/0142526 | A1 | * | 6/2006 | Lai | A61L 27/18 351/159.33 |
| 2007/0014755 | A1 | * | 1/2007 | Beckman | A61K 31/28 424/78.27 |
| 2007/0190229 | A1 | * | 8/2007 | Beckman | C08G 18/8025 427/2.1 |
| 2009/0005716 | A1 | * | 1/2009 | Abuzaina | A61L 24/001 602/43 |
| 2010/0029802 | A1 | * | 2/2010 | Mehrabi | A61K 31/695 522/170 |
| 2011/0015292 | A1 | * | 1/2011 | Radhakrishnan | C08G 18/12 521/170 |
| 2011/0301639 | A1 | * | 12/2011 | Beckman | A61L 24/046 606/213 |
| 2017/0056549 | A1 | * | 3/2017 | Clower | A61L 27/18 |

FOREIGN PATENT DOCUMENTS

| | | |
|---|---|---|
| EP | 0482467 A2 | 4/1992 |
| WO | 00/04069 A1 | 1/2000 |
| WO | 2009014886 A2 | 1/2009 |

OTHER PUBLICATIONS

International Search Report and Written Opinion in International Application No. PCT/US2016/049561, dated Dec. 8, 2016, 10 pages, See U.S. Appl. No. 15/252,275 for NPL.
International Preliminary Report on Patentability in International Application No. PCT/US2016/049561, dated Mar. 15, 2018, 8 pages.

* cited by examiner

*Primary Examiner* — Peter A Salamon
(74) *Attorney, Agent, or Firm* — DLA Piper LLP

(57) ABSTRACT

A composition that includes (a) a prepolymer having at least one free isocyanate group that is capable of bonding to tissue and that cures in vivo upon exposure to water to form a polymer having a compressive modulus between 1.9 and 14.4 MPa and a tensile modulus between 5.0 and 30, and (b) an oil that is miscible in the prepolymer, the oil being selected from the group consisting of silicone oils, mineral oil, vegetable oils, and combinations thereof. The composition retains its integrity when delivered in an aqueous medium.

9 Claims, No Drawings

MENISCAL REPAIR ADHESIVE

CLAIM OF PRIORITY

This application claims priority to U.S. Provisional Application Ser. No. 62/211,953, filed on Aug. 31, 2015, the entire contents of which are hereby incorporated by reference.

TECHNICAL FIELD

This invention relates to repairing tissue defects and injuries such as meniscal tears.

BACKGROUND

A meniscus is a C-shaped piece of cartilage located at the edge of the knee between the femur and tibia. Each knee has two menisci: one on the outer edge of the knee (lateral meniscus) and one on the inner edge of the knee (medial meniscus). A meniscal tear is a common injury that often occurs when the knee is twisted. As people age, the meniscus can also become worn and susceptible to tearing. Meniscal tears are typically treated through either open or arthroscopic surgery. In either case, the area typically is flooded with saline during the surgery.

SUMMARY

In one aspect, there is described a composition that includes (a) a prepolymer having at least one free isocyanate group that is capable of bonding to tissue and that cures in vivo upon exposure to water to form a polymer having a compressive modulus between 1.9 and 14.4 MPa and a tensile modulus between 5.0 and 30, and (b) an oil that is miscible in the prepolymer, the oil being selected from the group consisting of silicone oils, mineral oil, vegetable oils, and combinations thereof. The composition retains its integrity when delivered in an aqueous medium.

In certain embodiments, the prepolymer may include urethane linkages, urea linkages, or a combination thereof. Examples of suitable oils include silicone oils such as polydimethylsiloxane, simethicone, and combinations thereof.

In certain embodiments, the prepolymer is a siloxane prepolymer. An example of a suitable siloxane prepolymer has the formula:

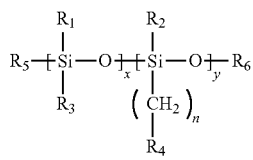

In this formula, n is 1 to 10; x and y, independently, are 2 to 10; $R^1$, $R^2$, $R^3$, $R^5$, and $R^6$, independently, are selected from the group consisting of hydroxyl groups; straight chain, branched, or cyclic $C_1$-$C_6$ alkyl groups that may be substituted with one or more isocyanate groups; straight chain, branched, or cyclic $C_1$-$C_6$ fluorinated alkyl groups that may be substituted with one or more isocyanate groups; and combinations thereof; $R^4$ is selected from the group consisting of —NCO, —SH, —OH, $R^7N^+X$—; $R^7$ is a straight chain, branched, or cyclic $C_1$-$C_6$ alkyl group; and X is selected from the group consisting of F, Cl, Br, and I, with the proviso that at least one of $R^1$, $R^2$, $R^3$, $R^4$, $R^5$, and $R^6$ includes an isocyanate group.

Another example of a suitable siloxane prepolymer has the following formula:

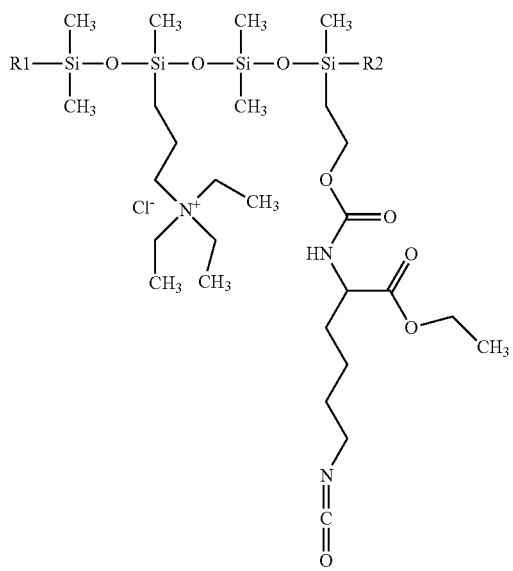

In this formula, $R^1$ and $R^2$, independently, are selected from the group consisting of hydroxyl groups; straight chain, branched, or cyclic $C_1$-$C_6$ alkyl groups that may be substituted with one or more isocyanate groups; straight chain, branched, or cyclic $C_1$-$C_6$ fluorinated alkyl groups that may be substituted with one or more isocyanate groups; and combinations thereof.

In certain embodiments, the prepolymer can include the reaction product of a polyisocyanate, an active hydrogen component selected from the group consisting of polyols, polyamines, polythiols, polycarboxylic acids, and combinations thereof, and, optionally, an ionic salt or amino acid component having an average hydroxyl or amino functionality, or combination thereof, of at least 1. Examples of suitable ionic salts components include ammoniates, halides, sulfonates, phosphonates, carboxylates, and combinations thereof. The composition may include at least two different prepolymers.

As used herein, the term "component" refers to single compounds, and to blends of different compounds.

Representative examples of suitable prepolymers having the following structures:

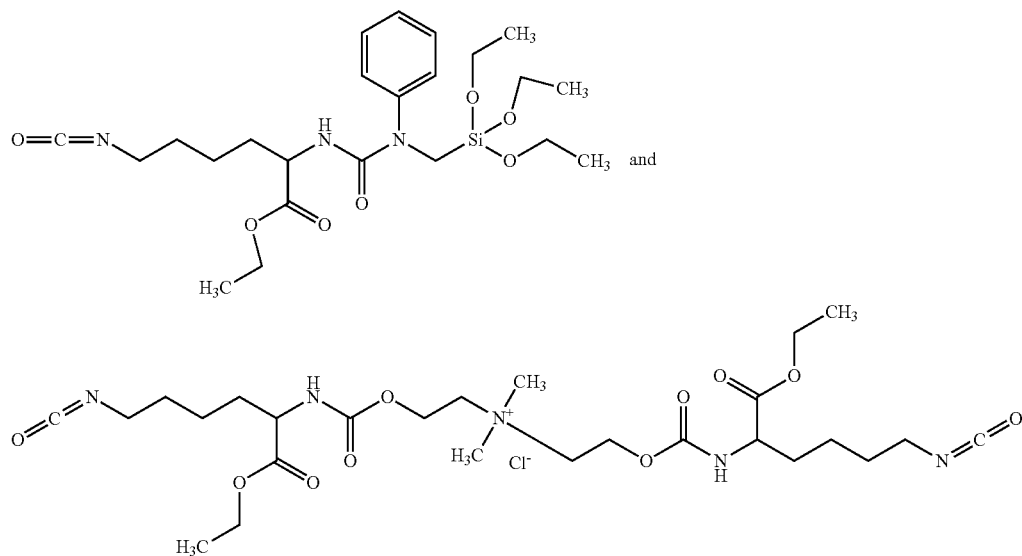

and

DETAILED DESCRIPTION

The compositions include (a) a prepolymer having at least one free isocyanate group that is capable of bonding to tissue and that cures in vivo upon exposure to water to form a polymer having a compressive modulus between 1.9 and 14.4 MPa and a tensile modulus between 5.0 and 30, and (b) an oil that is miscible in the prepolymer, the oil being selected from the group consisting of silicone oils, mineral oil, vegetable oils, and combinations thereof. The composition retains its integrity when delivered in an aqueous medium.

Because the compositions retain their integrity even when delivered in an aqueous environment, e.g., a saline solution, they remain intact and in place following delivery to the desired area of the tissue during surgery as the prepolymer cures and bonds to the tissue. In addition, the cured compositions are capable of withstanding the tensile, shear, and compressive forces to which they are exposed, e.g., within the knee joint. The specific cure times, viscosities, and mechanical properties can be tailored as necessary for individual applications.

Because the prepolymer includes at least one isocyanate group, it can bond to tissue, e.g., meniscal tissue, by reacting with surface groups on the tissue. In some cases, the release of controlled amounts of gas can create a scaffold-like structure and/or a textured surface that facilitates potential cell attachment and tissue regrowth through the cured polymer.

The composition may be used to repair a variety of tissues, including meniscal tissue, tendons, cartilage, and the like. For example, the composition may be used to repair a meniscal defect such as a tear by delivering the composition to a knee joint in an aqueous environment in the area of a meniscal defect, and allowing the composition to cure in the presence of water present in the knee joint. Because the composition retains its integrity even when immersed in an aqueous environment such as the saline environment typically encountered during surgery, it remains intact and in place following delivery to the desired area of the knee joint as it cures and bonds to the meniscal tissue.

The details of one or more embodiments of the invention are set forth in the description below. Other features, objects, and advantages of the invention will be apparent from the description and from the claims.

The oil in the composition contributes to the ability of the composition to retain its integrity when delivered in an aqueous environment. The oil may also perform the function of a defoaming agent.

In some embodiments, the compositions include siloxane prepolymers having the formula recited in the Summary of the Invention. Such prepolymers may be prepared e.g., by reacting alkoxy silanes and isocyanate-functional organosilanes.

Suitable alkoxy silane reactants have the formula: $(R^1R^2R^3)$—Si—$CH_2$—Z where (i) Z is an —OH, —SH, —NCO, or —$NHR^4$ group. $R^4$ is a hydrogen, an alkyl group (e.g., a $C_1$-$C_6$ alkyl group), or an aryl group (e.g., having at least one ring such as a phenyl group). Each $R^1$, $R^2$, and $R^3$, independently, is H, an alkoxy group (e.g., a $C_1$-$C_6$ alkoxy group), an alkyl group (e.g., a $C_1$-$C_6$ alkyl group), a heteroalkyl group other than an alkoxy group (e.g., an alkyl amido or amido group), an aryl group (e.g., a phenyl group), or a heteroaryl group (e.g., a pyrrolyl, furyl, or pyridinyl group), with the proviso that at least two of $R^1$, $R^2$, and $R^3$ are alkoxy groups. The alkyl groups may be straight chain, branched, or cyclic alkyl groups.

Suitable isocyanate-functional organosilane reactants have at least one free isocyanate group and at least one terminal silane group having the formula: $(R^5R^6R^7)$—Si— where each $R^5$, $R^6$, and $R^7$, independently, is H, an alkoxy group (e.g., a $C_1$-$C_6$ alkoxy group), an alkyl group (e.g., a $C_1$-$C_6$ alkyl group), a heteroalkyl group other than an alkoxy group (e.g., an alkyl amido or amido group), an aryl group (e.g., a phenyl group), or a heteroaryl group (e.g., a pyrrolyl, furyl, or pyridinyl group).

In some embodiments, the compositions include prepolymers prepared by reacting a polyisocyanate and an active hydrogen component. Examples of suitable active hydrogen components include hydroxyl-functional components, amine-functional components, thiol-functional components, carboxylic acid-functional components, and combinations thereof. In some embodiments, some or all of the functional groups may be primary groups.

One class of suitable active hydrogen components includes multi-functional alcohols selected from glycerol, di-glycerol, erythritol, pentaerythritol, xylitol, arabitol, fucitol, ribitol, sorbitol, mannitol, and combinations thereof. Also suitable are hydroxyalkyl derivatives and esters of any of these alcohols such as ethoxylated pentaerythritol.

Another class of suitable active hydrogen components includes hydroxyalkyl derivatives of $C_3$-$C_{10}$ carboxylic or dicarboxylic acids (e.g., dimethylol propionic acid, dimethylol butyric acid, and combinations thereof), and hydroxyalkyl derivatives of $C_3$-$C_{10}$ hydrocarbons (e.g., trimethylol propane).

The active hydrogen component can also be a hydroxalkyl amine (e.g., triethanolamine), a di-, tri-, or tetralkylene glycol, or combination thereof. Also suitable are hydroxyl-functional compounds selected from saccharides (e.g., glucose, fructose, sucrose, or lactose), oligosaccharides, polysaccharides, esters thereof, and combinations thereof.

The active hydrogen component can also be a polyamine or polyetheramine, e.g., Jeffamine.

An ionic salt or amino acid may also be included as a reactant in preparing the prepolymer. Suitable ionic salt reactants include one or more hydroxyl and/or amino functional groups. Consequently, they are able to react with isocyanate-functional components in the reaction mixture, and thereby become covalently incorporated in the prepolymer. Examples of suitable salts include ammoniates, halides, sulfonates, phosphonates, carboxylates, and combinations thereof. Specific examples include ammonium halides (e.g., ethyl triethanol ammonium chloride), choline halides (e.g., choline chloride), and combinations thereof. Examples of suitable amino acids include lysine, 1-arginine, and combinations thereof.

The composition may further include a catalyst. Examples of suitable catalysts include tertiary amines (e.g., aliphatic tertiary amines), organometallic compounds (e.g., bismuth salts and zirconium chelates), platinum, and palladium. Specific examples include 1,4-diazabicyclo[2.2.2]octane ("DABCO"), 2,2'dimorpholine diethyl ether ("DMIDEE"), dibutyltin dilaurate ("DBTDL"), bismuth 2-ethylhexanoate, bismuth neodecanoate, and combinations thereof. The amount of catalyst is selected based upon the particular reactants.

The composition may also include rheology-modifying agents such as a solvent and/or a non-volatile diluent. Examples of suitable solvents include dimethylsulfoxide (DMSO), dimethylformamide (DMF), tetrahydrofuran (THF), glyme, and combinations thereof. Examples of suitable non-volatile diluents include dimethylsulfoxide (DMSO), propylene carbonate, diglyme, polyethylene glycol diacetates, polyethylene glycol dicarbonates, dimethylisosorbide, ethyl pyruvate, triacetin, triethylene glycol and combinations thereof. A single reagent can perform multiple roles. Thus, for example, DMSO can function as both a solvent and a non-volatile diluent. The amount of the rheology modifying agent is selected based upon the constituents of the composition and the particular application for which it is being used.

The composition may also include antioxidants (e.g., BHT and BHA), water scavengers (e.g., acyl and aryl halides, and anhydrides), Bronsted acids, protonic acids (e.g., sulfuric or hydrochloric acid), and the like. The acids may also function as catalysts.

The composition may also include a colorant to help a surgeon visualize the composition during application to the meniscal tissue. An example of a suitable colorant is beta-carotene.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising:
(a) a siloxane prepolymer having at least one free isocyanate group that is capable of bonding to tissue and that cures in vivo upon exposure to water to form a polymer having a compressive modulus between 1.9 and 14.4 MPa and a tensile modulus between 5.0 and 30, and
(b) an oil that is miscible in the prepolymer, the oil being selected from the group consisting of silicone oils, mineral oil, vegetable oils, and combinations thereof, wherein the siloxane prepolymer has the formula:

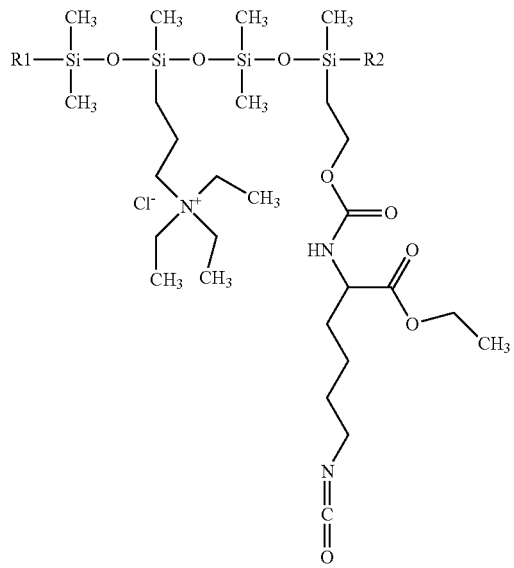

where $R^1$ and $R^2$, independently, are selected from the group consisting of hydroxyl groups; straight chain, branched, or cyclic $C_1$-$C_6$ alkyl groups that may be substituted with one or more isocyanate groups; straight chain, branched, or cyclic $C_1$-$C_6$ fluorinated alkyl groups that may be substituted with one or more isocyanate groups; and combinations thereof.

2. A composition according to claim 1 wherein the composition comprises at least two different prepolymers.

3. A composition according to claim 1 wherein the oil comprises a silicone oil.

4. A composition according to claim 3 wherein the silicone oil is selected from the group consisting of polydimethylsiloxane, simethicone, and combinations thereof.

5. A composition according to claim 1 wherein the tissue is selected from the group consisting of meniscal tissue, cartilage, tendons, and combinations thereof.

6. A method of repairing a defect in meniscal tissue comprising delivering a composition according to claim 1 to the knee joint in an aqueous environment in the area of the meniscal defect, and allowing the composition to cure and bond to the meniscal tissue.

7. A composition comprising:
(a) a prepolymer having at least one free isocyanate group that is capable of bonding to tissue and that cures in vivo upon exposure to water to form a polymer having a compressive modulus between 1.9 and 14.4 MPa and a tensile modulus between 5.0 and 30, and (b) an oil that is miscible in the prepolymer, the oil being selected from the group consisting of silicone oils, mineral oil, vegetable oils, and combinations thereof, wherein the prepolymer comprises the reaction product of (a) a polyisocyanate, (b) an active hydrogen component selected from the group consisting of polyols, polyamines, polythiols, polycarboxylic acids, and combinations thereof, and (c) an ionic salt or amino acid component having an average hydroxyl or amino functionality, or combination thereof, of at least 1, and the ionic salt component is selected from the group consisting of ammoniates, halides, sulfonates, phosphonates, carboxylates, and combinations thereof.

8. A composition according to claim 7 wherein the prepolymer is selected from the group of compounds having the formulae:

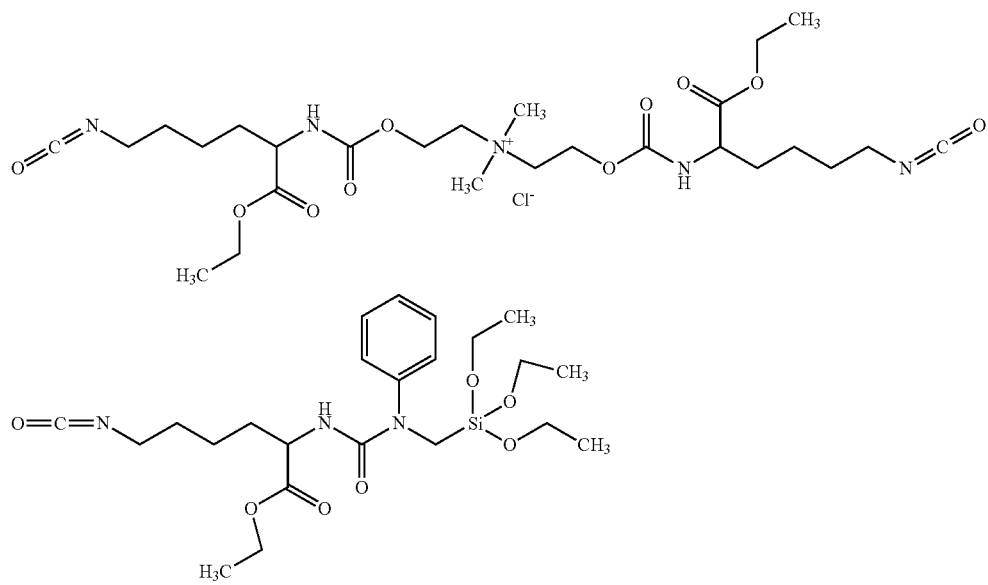

and combinations thereof.

9. A composition comprising:
(a) a prepolymer having at least one free isocyanate group that is capable of bonding to tissue and that cures in vivo upon exposure to water to form a polymer having a compressive modulus between 1.9 and 14.4 MPa and a tensile modulus between 5.0 and 30, and
(b) an oil that is miscible in the prepolymer, the oil being selected from the group consisting of silicone oils, mineral oil, vegetable oils, and combinations thereof, wherein the prepolymer is selected from the group of compounds having the formulae:

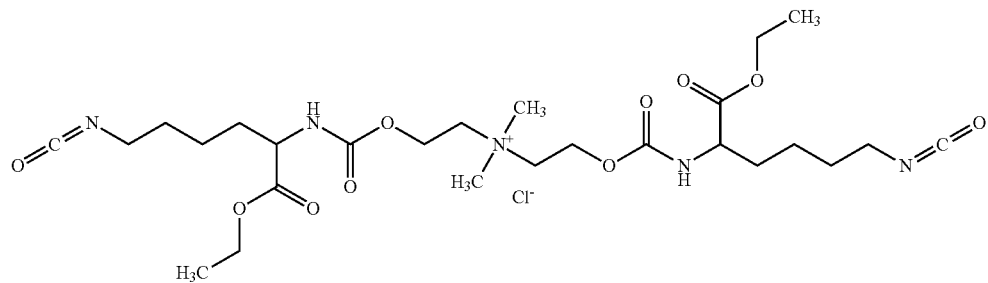

-continued
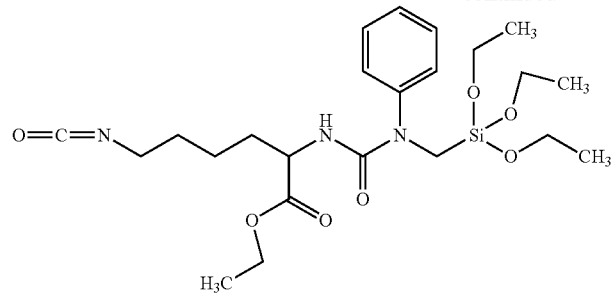
and combinations thereof.
* * * * *